(12) United States Patent
Miller

(10) Patent No.: US 8,278,089 B2
(45) Date of Patent: Oct. 2, 2012

(54) **QUALITY OF LIFE FOR HEPATITIS C PATIENTS WITH A FORMULATION FOR ADMINISTRATION TO THE ORAL MUCOSA INCLUDING *LACTOBACILLUS DELBRUECKII SUBSP. BULGARICUS* AND N-ACETYL D-GLUCOSAMINE**

(76) Inventor: Carl Miller, Houston, TX (US)

( * ) Notice: Subject to any disclaimer, the term of this patent is extended or adjusted under 35 U.S.C. 154(b) by 0 days.

(21) Appl. No.: 13/180,779

(22) Filed: Jul. 12, 2011

(65) Prior Publication Data

US 2011/0268829 A1 Nov. 3, 2011

Related U.S. Application Data

(63) Continuation of application No. 11/508,633, filed on Aug. 22, 2006, now Pat. No. 8,007,783.

(51) Int. Cl.
*C12N 1/20* (2006.01)
(52) U.S. Cl. ............... 435/252.9; 435/243; 424/93.45; 424/400; 424/464
(58) Field of Classification Search ............... 424/400, 424/464, 93.45; 435/243, 252.9
See application file for complete search history.

(56) References Cited

U.S. PATENT DOCUMENTS

| | | | | |
|---|---|---|---|---|
| 5,716,615 | A * | 2/1998 | Vesely et al. | 424/93.4 |
| 6,281,191 | B1 * | 8/2001 | Slesarev et al. | 514/3.7 |
| 6,767,557 | B2 * | 7/2004 | Ulrich et al. | 424/497 |
| 2004/0129174 | A1 * | 7/2004 | Li et al. | 106/162.8 |

* cited by examiner

*Primary Examiner* — Ruth Davis
(74) *Attorney, Agent, or Firm* — Gearhart Law, LLC

(57) ABSTRACT

Disclosed are quick dissolve tablets, each including *Lactobacillus delbrueckii* subsp *bulgaricus* (LBD) and N-acetyl-glucosamine (NAG), as well as excipients, for oral mucosal administration, for improving the quality of life of Hepatitis C patients. Any formulation suitable for oral mucosal administration can be employed for administering the active ingredients in a sufficient dosage for therapeutic effect, one such formulation being: 50 mg of *Lactobacillus delbrueckii* subsp *bulgaricus* lysate strain YB-I 10 mg of N-acetyl D-glucosamine. Excipients can include one or more of, maltodextrin; xanthan gum; acesulfam K; lemon powder and a flavoring, e.g., juice; Mannitol TL-32-04, Microcrystalline Cellulose and Carrageenan, Fructose, PVP-XL TL-11-04, Gellan Gum, Citrus TL 1-04, Orange TL 19-04, Sucrolose TL-13-04, and Mg ST TL-13-04.

11 Claims, No Drawings

QUALITY OF LIFE FOR HEPATITIS C PATIENTS WITH A FORMULATION FOR ADMINISTRATION TO THE ORAL MUCOSA INCLUDING *LACTOBACILLUS DELBRUECKII SUBSP. BULGARICUS* AND N-ACETYL D-GLUCOSAMINE

PRIORITY CLAIM

This application is a continuation application of application Ser. No. 11/508,633 filed on Aug. 22, 2006 and incorporated herein in its entirety by reference.

BACKGROUND

*Lactobacillus delbrueckii* subsp *bulgaricus* (LBD) is a gram-positive homofermentative lactic acid bacteria which metabolizes carbohydrates with lactic acid as the major end product (Salminen, S., and von Wright, A., "Current Probiotics-Safety Assured?" Microbial Ecology in Health and Disease (1998) 10:68-77).

LBD is well known as a food additive and dietary supplement, and is one of the components that are required by the FDA to be included in any product identified as "yogurt." LBD is a gram positive, non-motile, non-spore forming bacilli, which is homofermentative, and is almost exclusively present in milk (Germond, et al., Evoluton of the bacterial species Lactobacillus delbrueckii: A partial genomic study with reflections on prokaryotic species concept, Mol. Biol. Evol., 20(1):93-104, 2003; Pelczar, M. J. and Reid, R. D., Microbiology of Milk, Microbiology 2nd Edition, p. 534, McGraw Hill, NY, N.Y., 1965). For patients with hepatitis C, there are reports that administering LBD improves quality of life, and can even lower viral load.

In fact, it has been postulated that LDB may work therapeutically by improving the immunologic barrier of the intestine through stimulating the immunoglobulin A response or by alleviating the inflammatory response (Isolaurie et al., Probiotics: effect on immunity, Amer. J. Clin. Nutr. (2001) 73(suppl):444S-450S). Anti-inflammatory properties of fermented milk on the intestine may be derived from their ability to inhibit platelet activating factor (P AF), a potent phospholipids mediator secreted by pro inflammatory cells. LDB was found to be a critical component in the biosynthesis of quantities of P AF inhibitors (Heyman, M., Effect of Lactic Acid Bacteia on Diarrheal Diseases, J Amer College of Nutr (2000) 19(2):137S-146S). Studies have reported the increase in cytokines such as the cytokines I1-10 and I1-4 in mice (Ghosh et al., Probiotics in inflammatory bowel disease: is it all gut flora modulation?, Gut (2004) 53:620-622) as well as activation of macrophages following the oral introduction of LDB (Isolauri, E. et al., supra) and the stimulation of IFN-alpha/beta following intraperitoneal injection of LDB in animal studies (Pereyra et al., Interferon induction by Lactobacillus bulgaricus and Streptococcus thermophilus in mice, Eur Cytokine News (1991) 2(4):299-303). LDB has also been investigated in vivo and in vitro for toxicity towards the carcinogens MNNG and H202. Acetone extracts of LDB as well as lactic acid metabolites that were expected to be in the gut lumen as fermentation products were examined. LDB (but not the metabolites) was determined to be antigenotoxic (Wollowski et al., Bacteria Used for the Production of Yogurt Inactivate Carcinogens and Prevent DNA Damage in the Colon of Rats, J. Nutr (1999) 129:77-82).

N-acetyl-glucosamine (NAG) is a compound that exists naturally in the body. In various forms, this compound has been studied for its potential in alleviating some of the conditions associated with several diseases including osteoarthritis, inflammatory bowel disease and Crohn's disease and the inflammatory response in peritonitis (Gardiner, Dietary N-acetylglucosamine (GlcNAc): Absorption, Distribution, Metabolism, Excretion and Biological Activity, Glyco-Science and Nutrition (2000) 1(9):1-3; Salvatore et al., A pilot Study of N-acetyl-glucosamine, a nutritional substrate for glycosaminoglycan synthesis in paediatric chronic inflammatory bowel disease, Alimentary Pharmacology and Therapeutics (2000) 14(12):1567-1579). LBD in combination with NAG has been suggested as a treatment for Hepatitis C (U.S. Pat. No. 6,281,191).

SUMMARY

Disclosed are quick dissolve tablets, each including Lactobacillus delbrueckii subsp bulgaricus (LBD) and N-acetylglucosamine (NAG), as well as excipients, for oral mucosal administration. Any formulation suitable for oral mucosal administration can be employed for administering the active ingredients in a sufficient dosage for therapeutic effect, one such formulation being: 50 mg of Lactobacillus delbrueckii subsp bulgaricus lysate strain YB-I ("LB YB-I") (available from Kerry BioScience, Schaumburg, Ill.) 10 mg of N-acetyl D-glucosamine (NAG). Preferred excipients are, maltodextrin; xanthan gum; acesulfam K; lemon powder and a flavoring, e.g., juice. When prepared as described herein, a tablet is generated which dissolves in the mouth in 30 to 45 seconds, although any tablet or formulation capable of dissolving on the oral mucosa in less than about one minute is acceptable.

Clinical trials are underway to determine the effect of this formulation on quality of life for Hepatitis C infected patients. The SF-36 score measures the quality of life for patients, based on a self-administered scoring system that includes eight independent scales and two main dimensions. It has been widely used and validated. An increase in quality of life of two points or more on the SF-36 scoring system, over the course of six months of administration of the formulation, is scored as improvement in the clinical trial.

DETAILED DESCRIPTION

In order to generate the formulation described herein suitable for therapy, which is capable of dissolving on the oral mucosa in less than about one minute and releasing the active ingredients, the following exemplary procedure may be followed, although there are a number of other processes which could also generate a suitable formulation. The process consists of three steps of processing the active ingredients and two steps involving formulation and tablet making.

1. Active Ingredient Process

Fermentation

Cells of *Lactobacillus delbrueckii* subsp. *Bulgaricus* (strain YB-1 from Kerry Bioscience) are fermented in 500 L of an appropriate media for approximately 120 hours.

Cell Isolation

The 500 L of broth is centrifuged and the resultant cell mass is washed three times with DI water. This produces approximately 60 kgs of wet cell mass.

Lysing and Purification

The wet cell mass is reconstituted and the pH is adjusted to 6.8-7.0. Lysozyme chloride (extracted from hen egg whites) is added to make a solution with a concentration of 500 ppm of lysozyme chloride. The slurry is agitated and the temperature is maintained at 40-50° C. for 24 hours. After lysing, the active components are in the liquid phase. This liquid material containing the water soluble active components is recovered through centrifugation to remove the solid material, and then washed three times with DI water. The resultant mixture is frozen in pellets and the remaining solid material in the centrifuge is discarded.

2. Formulation and Tableting

The frozen pellets are freeze dried to form a dry powder and milled, if necessary. This material is blended with excipients and N-acetyl D-glucosamine HCl (NAG) to form a mixture of 52 mgs lysed LDB and 13 mgs NAG, per pellet. Purified water is added to the blended mixture in preparation for making the quick dissolve tablets. Approximately 180 mgs of the solution of LDB, NAG, and excipients (e.g., maltodextrin; xanthan gum; acesulfam K; lemon powder and a flavoring) are added to preformed 2 ml wells in PVC plastic stock and then placed in a lyophilization chamber. After lyophilization, the PVC plate is removed and lid stock is applied to form a sealed product.

The tablet is a gray, in the shape of the plastic well, with a mirror finish on the side next to the plastic stock and rough appearance on the top. When placed on the tongue, and not chewed or swallowed, the tablet dissolves in 30-45 seconds.

Another exemplary formulation for a quick dissolve tablet for administering the active ingredients through the oral mucosa includes the following ingredients in the following proportions:

TABLE I

| Mannitol TL-32-04 | 52.8% |
| Microcrystalline Cellulose and Carrageenan | 15.0% |
| Fructose | 12.5% |
| PVP-XL TL-11-04 | 5.0% |
| LBD (four parts); NAG (one part) | 9.1% |
| Gellan Gum | 0.5% |
| Citrus TL 1-04 | 3.0% |
| Orange TL 19-04 | 1.0% |
| Sucrolose TL-13-04 | 0.5% |
| MgST TL-13-04 | 0.6% |

It can be formulated according to methods known to those skilled in the art.

It should be understood that the terms, expressions, procedures and examples herein are exemplary only, and not limiting, and that the scope of the invention is defined only in the claims which follow, and includes all equivalents of the subject matter of the claims.

What is claimed is:

1. A formulation to treat Hepatitis C infected patients, active ingredients of said formulation consisting essentially of: *Lactobacillus delbrueckii* subsp *bulgaricus* freeze dried lysate, and N-acetyl-glucosamine; and
   said formulation dissolving on oral mucosa and releasing the active ingredients in less than about one minute following administration.

2. The formulation of claim 1, wherein the *Lactobacillus delbrueckii* subsp *bulgaricus* lysate is strain YB-I.

3. The formulation of claim 2, wherein the formulation has 50 mg of *Lactobacillus delbrueckii* subsp *bulgaricus* lysate strain YB-I and 10 mg of N-acetyl D-glucosamine.

4. The formulation of claim 3, wherein the formulation further includes excipients.

5. The formulation of claim 4, wherein the excipients are maltodextrin; xanthan gum; acesulfame K; lemon powder and a flavoring.

6. The formulation of claim 4, wherein the excipients are Mannitol, Microcrystalline Cellulose and Carrageenan, Fructose, PVP, Gellan Gum, Citrus-flavor Sucralose, and Mg stearate.

7. The formulation of claim 1, wherein treating patients results into an improvement in quality of life indicated by a two point or greater improvement in SF-36 scores.

8. The formulation of claim 1, wherein the formulation is a tablet and dissolves within 30 to 45 seconds following administration.

9. A fast dissolving tablet for treating Hepatitis C infected patients, said tablet consisting of active ingredients and excipients, said active ingredients being four parts of *Lactobacillus delbrueckii* subsp *bulgaricus* freeze dried lysate, and one part of N-acetyl-glucosamine.

10. The tablet of claim 9, wherein the tablet consists of 9.1% of active ingredients, 52.8% of mannitol, 15.0% of microcrystalline cellulose and carrageenan, 12.5% of fructose, 5.0% of PVP, 0.5% of Gellan Gum, 3.0% of Citrus flavor, 1.0% Orange-flavor 0.5% Sucralose and 0.6% of Mg stearate.

11. A formulation to improve quality of life of Hepatitis C patients by a two point or greater improvement in SF-36 scores, active ingredients of said formulation consisting essentially of:
   *Lactobacillus delbrueckii* subsp *bulgaricus* freeze dried lysate, and N-acetyl-glucosamine; and
   said formulation dissolving on oral mucosa and releasing the active ingredients in less than about one minute following administration.

* * * * *